US012751979B2

(12) United States Patent
Sohn

(10) Patent No.: US 12,751,979 B2
(45) Date of Patent: Oct. 6, 2026

(54) COMPOSITION FOR PREVENTING OR TREATING INFLAMMATORY BOWEL DISEASE

(71) Applicant: AJOU UNIVERSITY INDUSTRY-ACADEMIC COOPERATION FOUNDATION, Suwon-si (KR)

(72) Inventor: Seong Hyang Sohn, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 762 days.

(21) Appl. No.: 18/015,868

(22) PCT Filed: Jun. 25, 2021

(86) PCT No.: PCT/KR2021/007993

§ 371 (c)(1),
(2) Date: Jun. 5, 2023

(87) PCT Pub. No.: WO2022/014893

PCT Pub. Date: Jan. 20, 2022

(65) Prior Publication Data

US 2024/0277785 A1 Aug. 22, 2024

(30) Foreign Application Priority Data

Jul. 13, 2020 (KR) ........................ 10-2020-0086001
Jun. 22, 2021 (KR) ........................ 10-2021-0080591

(51) Int. Cl.

| | |
|---|---|
| ***A61K 35/741*** | (2015.01) |
| ***A61K 35/00*** | (2006.01) |
| ***A61K 35/744*** | (2015.01) |
| ***A61K 35/747*** | (2015.01) |
| ***A61P 37/06*** | (2006.01) |

(52) U.S. Cl.

CPC .......... *A61K 35/741* (2013.01); *A61K 35/744* (2013.01); *A61K 35/747* (2013.01); *A61P 37/06* (2018.01); *A61K 2035/115* (2013.01)

(58) Field of Classification Search

None

See application file for complete search history.

(56) References Cited

U.S. PATENT DOCUMENTS

| | | | |
|---|---|---|---|
| 2018/0169153 | A1 | 6/2018 | Berry et al. |
| 2019/0262407 | A1 | 8/2019 | Dutta |

FOREIGN PATENT DOCUMENTS

| | | | |
|---|---|---|---|
| CN | 102670663 B | 10/2014 |
| KR | 10-2011-0125667 A | 11/2011 |
| KR | 10-2013-0087238 A | 8/2013 |
| KR | 10-2018-0053764 A | 5/2018 |
| KR | 10-2020-0021257 A | 2/2020 |
| KR | 10-2020-0039319 A | 4/2020 |
| KR | 10-2020-0040051 A | 4/2020 |
| WO | WO 2012/142605 A1 | 10/2012 |
| WO | WO 2019/118515 A2 | 6/2019 |

OTHER PUBLICATIONS

Kumazawa et al., "Isolation of immune-regulatory Tetragenococcus halophilus from miso", PLOS One, vol. 13(12), article e0208821, pp. 1-19. (Year: 2018).*

Kawashima, Tadaomi, et al., "Double-Stranded RNA of Intestinal Commensal but Not Pathogenic Bacteria Triggers Production of Protective Interferon-β", Immunity, Jun. 27, 2013, (11 Pages in English).

Cheng, Yingzhou, et al., "Effects of Lactobacillus animalis LGM on transcription factors gene expressions in DSS-induced colitis mice", Jun. 14, 2019, (8 Pages in Chinese and 6 Pages in English).

* cited by examiner

*Primary Examiner* — Grant C Currens
(74) *Attorney, Agent, or Firm* — NSIP Law

(57) ABSTRACT

The present invention relates to a composition for preventing or treating inflammatory bowel disease. More specifically, the present invention provides a pharmaceutical composition and a health food composition for preventing or treating inflammatory bowel disease, comprising, as active ingredients, two or more strains selected from the group consisting of *Tetragenococcus halophilus, Eubacterium rectale*, and *Lactobacillus animalis*; and cultures of the strains, concentrates of the cultures, extracts of the cultures, or lysates thereof. The composition comprises two or more strains having anti-inflammatory activity as an active ingredient and regulates immune cells related to inflammatory bowel disease, thereby preventing, ameliorating or treating inflammatory bowel disease more effectively than a single strain.

5 Claims, 9 Drawing Sheets

COMPOSITION FOR PREVENTING OR TREATING INFLAMMATORY BOWEL DISEASE

CROSS REFERENCE TO RELATED APPLICATIONS

This application is a U.S. National Stage Application of International Application No. PCT/KR2021/007993, filed on Jun. 25, 2021, which claims the benefits under 35 USC 119(a) and 365(b) of Korean Patent Application No. 10-2020-0086001, filed on Jul. 13, 2020 and Korean Patent Application No. 10-2021-0080591 filed on Jun. 22, 2021 in the Korean Intellectual Property Office, the entire disclosure of which is incorporated herein by reference for all purposes.

TECHNICAL FIELD

The present disclosure relates to a composition for preventing or treating an inflammatory bowel disease, and specifically, a composition for preventing or treating an inflammatory bowel disease including two or more strains as active ingredients.

BACKGROUND ART

Inflammatory bowel disease (IBD) is a disease with repetitive amelioration and recurrence of abnormal chronic inflammation in the intestinal tract, typical examples of which are ulcerative colitis and Crohn's disease, with no clear pathogenesis revealed yet. The diagnosis of inflammation is carried out by combining clinical symptoms, endoscopic and histopathological findings, blood test findings, and radiological findings. Inflammatory bowel disease is a chronic disease in which a remission period where symptoms disappear and a relapse period where the symptoms worsen alternate, the treatment of which is mainly aimed at controlling symptoms, preventing complications, and improving quality of life rather than complete cure of the disease.

Crohn's disease is an inflammatory disease occurring in the digestive organ ranging from the oral cavity to the anus with an unknown cause and accompanied by weight loss due to abdominal pain and diarrhea, and remission and deterioration repeat. The exact cause of ulcerative colitis has not been known yet, but genetic predisposition, intestinal microflora, and immunological abnormalities are complexly involved to cause chronic inflammation in the large intestine, accompanied by repetitive remission and deterioration.

It is necessary to identify the mechanism of occurrence and control of an inflammatory bowel disease and develop new therapeutics that may effectively treat an inflammatory bowel disease through controlling of related factors.

DISCLOSURE OF THE INVENTION

Technical Goals

An object of the present disclosure is to provide a pharmaceutical composition and a health food composition, including strains effective in preventing, ameliorating, or treating an inflammatory bowel disease.

Technical Solutions

To achieve the above object, the present disclosure provides a pharmaceutical composition for preventing or treating an inflammatory bowel disease, including, as active ingredients, two or more strains selected from the group consisting of *Tetragenococcus halophilus, Eubacterium rectale*, and *Lactobacillus animalis*; and cultures of the strains, concentrates of the cultures, extracts of the cultures, or lysates thereof.

In addition, the present disclosure provides a health food composition for preventing or ameliorating an inflammatory bowel disease, including, as active ingredients, two or more strains selected from the group consisting of *Tetragenococcus halophilus, Eubacterium rectale*, and *Lactobacillus animalis*; and cultures of the strains, concentrates of the cultures, extracts of the cultures, or lysates thereof.

Advantageous Effects

A composition according to the present disclosure includes two or more strains exhibiting anti-inflammatory activity as active ingredients and regulates immune cells related to an inflammatory bowel disease, thereby preventing, ameliorating, or treating an inflammatory bowel disease more effectively than a single strain.

In addition, by combining with existing therapeutic agents, the therapeutic effect of the composition may be further enhanced.

BEST MODE FOR CARRYING OUT THE INVENTION

Figure 1:
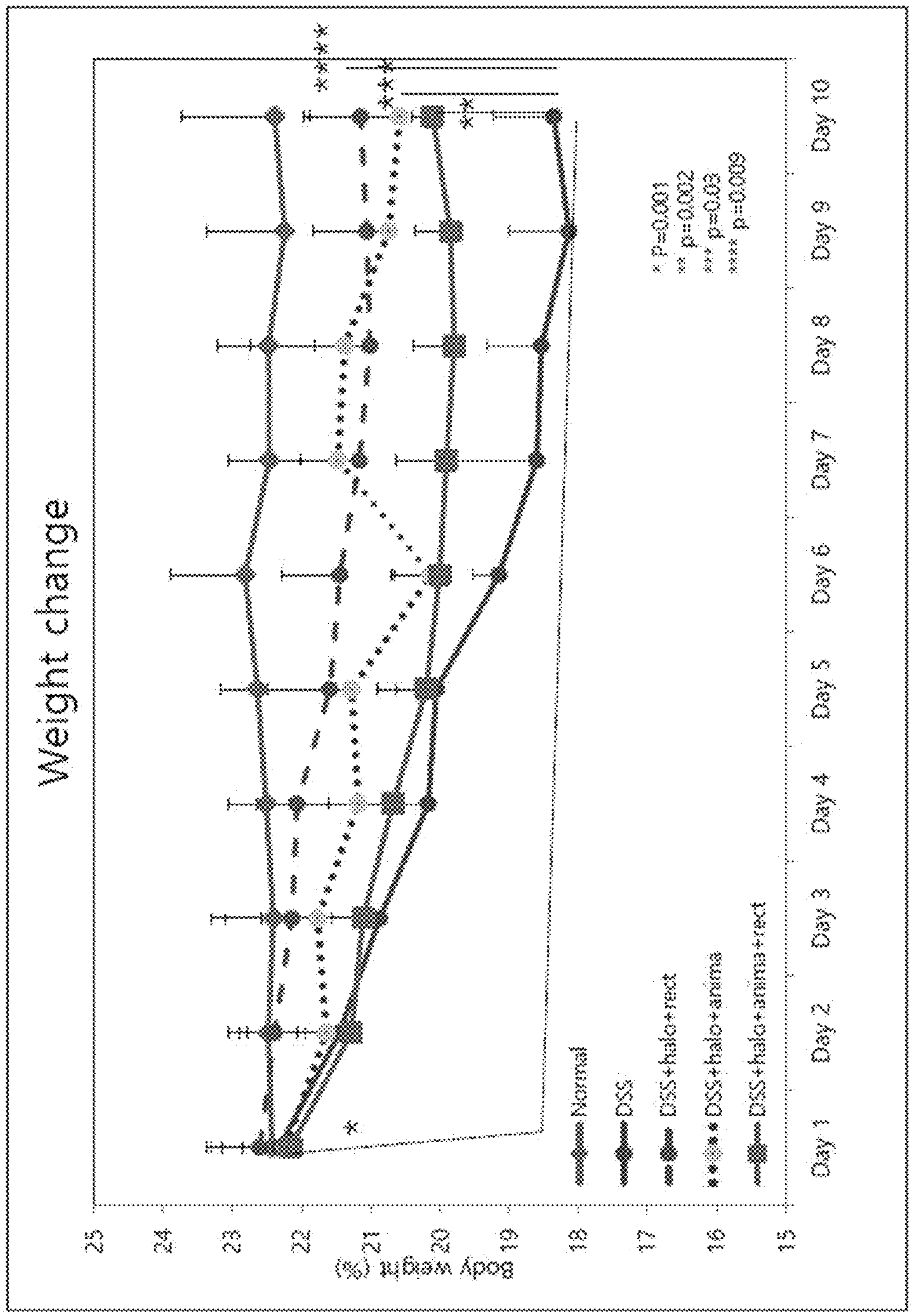
FIG. 1 shows a graph illustrating weight changes of a dextran sulfate sodium salt (DSS)-induced enteritis mouse model according to an example embodiment of the present disclosure.

Hereinafter, the present disclosure will be described in detail.

The present inventor completed the present disclosure by finding that, when various strains were orally administered in the process of inducing enteritis with dextran sulfate sodium salt (DSS), the symptom of enteritis in mice was alleviated, such that the strain or a combination thereof may be applicable as a therapeutic agent or therapeutic adjuvant for an inflammatory bowel disease such as Crohn's disease or ulcerative colitis.

The present disclosure provides a pharmaceutical composition for preventing or treating an inflammatory bowel disease, including, as active ingredients, two or more strains selected from the group consisting of *Tetragenococcus halophilus, Eubacterium rectale*, and *Lactobacillus animalis*; and cultures of the strains, concentrates of the cultures, extracts of the cultures, or lysates thereof.

As used herein, "*Tetragenococcus halophilus* (*T. halophilus*)" refers to a halophilic lactic acid bacterium (LAB) found in the fermentation process such as soy sauce, fermented soybean paste, fish sauce, and salted anchovies, and is also known as *Pediococcus halophilus*.

*Tetragenococcus halophilus* is a gram-positive coccus with a size of 0.6 to 1 μm and has no motility, without forming spores. The *Tetragenococcus halophilus*, a plant-derived lactic acid bacterium, may well stand against acidic digestive juices in the stomach or small intestine compared to animal-derived lactic acid bacteria inhabiting in animal foods such as milk and yogurt, and shows effects, such as promoting intestinal activity, enhancing immunity, and eliminating harmful bacteria in the intestine, comparable to those of animal-derived lactic acid bacteria, with viability over 400 times stronger. In addition, the plant-derived lactic acid bacteria have more than 8 times the ability to eliminate aflatoxin, a toxin derived from mold, compared to animal-derived lactic acid bacteria.

As used herein, "*Eubacterium rectale* (*E. rectale*)" refers to a microorganism which is one of species of *Eubacterium* and one of the most abundant bacteria in human feces, and also has been found in association with rectal ulcers. The *Eubacterium* is in the genus of gram-positive anaerobic *bacillus* and isolated as normal flora from feces, rumen, and periodontal tissues. The cell morphology of the *Eubacterium* is uniform or multimorphic, without forming spores. The optimal growth temperature for the *Eubacterium* is 37° C., and the optimum pH is 7.0.

As used herein, "*Lactobacillus animalis* (*L. animalis*)" is one of the most common lactic acid bacteria generated in the process of preparing kimchi, a traditional Korean food. *Lactobacillus*, a gram-positive, facultative anaerobic or microaerophilic bacterium that ferments sugars to obtain energy and produce large amounts of lactic acid, is a rod-shaped aposporous *bacillus*, while showing polymorphism. The size of *Lactobacillus* is 0.5~0.9×1~11 μm, showing various morphologies including the short rod and the long rod, most of which are immotile, prefer growing in low-oxygen environment, and produce lactic acid from various sugars.

In the present disclosure, the composition may include two or more strains selected from the group consisting of *Tetragenococcus halophilus, Eubacterium rectale*, and *Lactobacillus animalis*, preferably all of *Tetragenococcus halophilus, Eubacterium rectale*, and *Lactobacillus animalis*, but is not limited thereto.

More preferably, the composition may include *Tetragenococcus halophilus, Eubacterium rectale*, and *Lactobacillus animalis* in a bacterial count ratio of 1:(2 to 5):(0.2 to 0.6), preferably in a bacterial count ratio of 1:(3 to 4):(0.3 to 0.5), but is not limited thereto.

By including two or more of the strains, the composition may further enhance the ameliorating or therapeutic effects for an inflammatory bowel disease.

In addition to the strains, the composition may include cultures of the strains, concentrates of the culture, extracts of the culture, or lysates thereof.

The culture may include a culture medium itself cultured in a medium as well as processed products derived from the culture medium itself such as filtrates from which the strain was removed by filtering or centrifuging the culture medium, concentrates and extracts thereof.

The lysate may include a lysate obtained by disrupting the strain and a supernatant obtained by centrifuging the lysate. In addition, the composition may include a mixture of live, i.e., active strains and killed strains, but is not limited thereto.

The composition may further include one or more suitable prebiotic compounds.

As used herein, "prebiotic compound" refers to a non-digestible component that increases the growth of certain microorganisms in the gastrointestinal tract and a nutrient source for probiotics (beneficial bacteria) to activate probiotics or increase the number of strains. The prebiotic compound may be resistant to hydrolysis as well as digestion and absorption by enzymes such as gastric acid of mammals, fermented by the action of the probiotics, and become a substance that selectively stimulates the proliferation and activity of the probiotics.

The prebiotic compound is generally a non-digestible carbohydrate such as oligo-polysaccharide, or sugar alcohol, and it may include, for example, one or more selected from the group consisting of fructo-oligosaccharide (FOS), isomalto-oligosaccharide (IMO), xylo-oligosaccharide (XOS), chito-oligosaccharide (COS), pectin, inulin, β-glucan, polydextrose, D-tagatose, and acacia fibers.

The amount to be included and the activity of the prebiotic compound may vary depending on the species, types, and combination of the probiotics. For example, the composition may include the prebiotic compound in an amount of about 1 to about 30 wt % with respect to 100 wt % of the total composition, preferably in an amount of 5 to 20 wt %, and the activity of the strains may be different by the prebiotic compound.

In the present disclosure, the composition may regulate expression of one or more immune cells whose phenotypes are selected from the group consisting of CD11b+, Ly6G+, CD8+NK1.1+, CD11b+Ly6G+, and CD80+, preferably, it may reduce or inhibit the immune cells or reduce expression of the CD11b+, Ly6G+, CD8+NK1.1+, CD11b+Ly6G+, and CD80+.

According to an example embodiment of the present disclosure, since the strains reduce immune cells associated with inflammation and expression of activating molecules thereof, it is determined that anti-inflammatory activity is ensured.

In the present disclosure, the inflammatory bowel disease may be one or more selected from the group consisting of ulcerative colitis, Crohn's disease, Behcet's enteritis, infectious enteritis, radiation enteritis, ischemic bowel disease, and irritable bowel syndrome, but is not limited thereto.

The infectious enteritis may include bacterial, viral, amoebic, or tuberculous enteritis, but is not limited thereto.

The pharmaceutical composition according to the present disclosure may be prepared according to conventional methods in the pharmaceutical field. The pharmaceutical composition may be combined with a pharmaceutically acceptable suitable carrier depending on the formulation, and may be prepared by further including an excipient, diluent, dispersant, emulsifier, buffer, stabilizer, binder, disintegrant, and solvent, as needed. The suitable carrier does not interfere with the activity and characteristics of the strains according to the present disclosure and may be selected differently according to the dosage form and formulation.

The pharmaceutical composition may be applied in any formulation, and more specifically, it may be formulated and used in oral formulations as well as parenteral formulation of external agents, suppositories, and sterile injection solutions according to conventional methods.

The solid formulation of the oral formulation is in the form of tablets, pills, acids, granules, gels, and capsules and may be prepared by mixing at least one or more excipients, such as starch, calcium carbonate, sucrose, lactose, sorbitol, mannitol, cellulose, and gelatin, and lubricants such as magnesium stearate and talc may be included in addition to simple excipients. In addition, in the case of the capsule formulation, a liquid carrier such as fatty oil may be further included, in addition to the above-mentioned substances.

Liquid formulation among the oral formulations may include a suspension, solution, emulsion, and syrup, and various excipients such as a wetting agent, sweetener, fragrance, and preservative may be included in addition to commonly used simple diluents such as water and liquid paraffin.

The parenteral formulation may include a sterilized aqueous solution, non-aqueous solvent, suspension, emulsion, lyophilized agent, and asuppository. As the non-aqueous solvent and suspension, propylene glycol, polyethylene glycol, vegetable oils such as olive oil, and injectable esters such as ethylolate may be used. Witepsol, macrogol, Tween 61, cacao butter, laurin fat, and glycerogelatin may be used as a base of the suppositories. Without limitation, all suitable preparations known in the art may be used.

In addition, the pharmaceutical composition according to the present disclosure may be further added with calcium or vitamins to enhance the therapeutic efficacy.

The pharmaceutical composition according to the present disclosure may be administered in a pharmaceutically effective amount.

As used herein, the term “pharmaceutically effective amount” refers to an amount sufficient to treat a disease at a reasonable benefit/risk ratio applicable to medical treatment without causing adverse effects.

The effective dose level of the pharmaceutical composition may be differently determined depending on the purpose of use, the age, sex, weight and health status of a patient, the type of disease, the severity, the activity of a drug, the sensitivity to a drug, the administration method, the duration of administration, the administration route and excretion rate, the treatment period, factors including drugs combined or used in combination with, and other factors well known in the medical field. For example, a suitable daily dose of bacteria for an adult human may be about $1\times10^3$ to about $1\times10^{11}$ CFU (colony forming unit), for example, about $1\times10^6$ to about $1\times10^{10}$ CFU, in another example, about $1\times10^7$ to about $1\times10^8$ CFU.

The pharmaceutical composition may be administered individually or in combination with other therapeutic agents and administered sequentially or simultaneously with conventional therapeutic agents. It may also be administered single or multiple times. Considering all the factors above, it is important to administer an amount that the maximum effect may be derived with the minimum amount without side effects.

The pharmaceutical composition may be administered to any animal in which an inflammatory bowel disease may occur, and the animal may include, for example, humans and primates as well as livestock such as cattle, pigs, horses, and dogs.

The pharmaceutical composition may be administered by a suitable route of administration according to the preparation form and administered through various routes such as oral or parenteral, as long as it may reach the desired tissue. The administration method may be administered in conventional ways without particular limitation, such as oral, rectal or intravenous, intramuscular, skin application, respiratory inhalation, and intrauterine dural or intracere-broventricular injection.

The pharmaceutical composition may be used alone for prevention or treatment of an inflammatory bowel disease or in combination with surgery or other drug treatments, and it may be particularly effective when used in combination with compounds commonly used in the treatment of an inflammatory bowel disease, such as antibiotics, anti-inflammatory agents, anesthetics, and analgesics.

The present disclosure provides a health food composition for preventing or ameliorating an inflammatory bowel disease, including, as active ingredients, two or more strains selected from the group consisting of *Tetragenococcus halophilus, Eubacterium rectale*, and *Lactobacillus animalis*; and cultures of the strains, concentrates of the cultures, extracts of the cultures, or lysates thereof.

The corresponding features may be substituted in the above-described part.

The health food according to the present disclosure may be prepared as a powder, granule, tablet, capsule, syrup, or beverage for the purpose of preventing or ameliorating an inflammatory bowel disease. The form that the health food may take is not limited, and the health food may be prepared in the same manner as the pharmaceutical composition to be used as a functional food or added to various foods.

The health food may include all foods in the conventional sense. For example, beverages and various drinks, fruits and processed foods thereof (canned fruits, jams, etc.), fish, meat and processed foods thereof (ham, bacon, etc.), breads and noodles, cookies and snacks, and dairy products (butter, cheese, etc.) may be possible, and all functional foods in the conventional sense may be included. It may also include food used as feed for animal.

The health food composition may be prepared by further including sitologically acceptable food additives and other suitable auxiliary ingredients commonly used in the art. The suitability as the food additive may be determined by the standards and criteria related to corresponding items according to the general rules and general test methods of Korean Food Additives Codex approved by the Ministry of Food and Drug Safety, unless otherwise stipulated. The items listed in the ‘Korean Food Additives Codex’ may include, for example, chemical compounds such as ketones, glycine, calcium citrate, nicotinic acid, and cinnamic acid; natural additives such as persimmon color, licorice extracts, crystallized cellulose, kaoliang color, and guar gum; and mixed preparations such as sodium L-glutamate preparations, noodle-added alkali agents, preservative agents, and tar color agents.

The other auxiliary ingredients may further include, for example, flavoring agents, natural carbohydrates, sweeteners, vitamins, electrolytes, colorants, pectic acids, alginic acid, organic acids, protective colloidal thickeners, pH adjusters, stabilizers, preservatives, glycerin, alcohols, and carbonating agents. In particular, as the natural carbohydrate, monosaccharides such as glucose and fructose, disaccharides such as maltose and sucrose, and polysaccharides such as dextrin and cyclodextrin, and sugar alcohols such as xylitol, sorbitol, and erythritol may be used, and natural sweeteners such as taumatin and stevia extract or synthetic sweeteners such as saccharin and aspartame may be used as sweeteners.

The effective dose of the strains included in the health food may be appropriately adjusted according to the purpose of use, such as prevention or amelioration of an inflammatory bowel disease.

The health food composition is based on food such that there is no side effect that may occur in the long-term administration of general drugs, has the advantage of providing nutritional benefits, is highly portable, and may be consumed as an adjuvant for prevention or amelioration of an inflammatory bowel disease.

In addition, the present disclosure provides a composition for enhancing the therapeutic effect of a therapeutic agent for an inflammatory bowel disease, including, as active ingredients, two or more strains selected from the group consisting of *Tetragenococcus halophilus, Eubacterium rectale*, and *Lactobacillus animalis*; and cultures of the strains, concentrates of the cultures, extracts of the cultures, or lysates thereof.

The corresponding features may be substituted in the above-described part.

MODES FOR CARRYING OUT THE INVENTION

Hereinafter, to help the understanding of the present disclosure, example embodiments will be described in detail. However, the following example embodiments are merely illustrative of the contents of the present disclosure, and the scope of the present disclosure is not limited to the following example embodiments. Example embodiments of the present disclosure are provided to more fully explain the present disclosure to those skilled in the art.

<Example 1> Preparation of Strain

The strains used in the following experimental examples were obtained from KCTC and ATCC.

*Tetragenococcus halophilus*: KCTC #3720

*Lactobacillus animalis*: KCTC #3501

*Eubacterium rectale*: ATCC 33656™, KCTC #5835

<Example 2> Identification of Therapeutic Effect on Inflammatory Bowel Disease After administering bacterial strains according to the Example 1 to a dextran sulfate sodium salt (DSS)-induced enteritis mouse model, weight changes and immune cell phenotypes were checked to identify suppression on exacerbation of symptoms of DSS-induced enteritis and immune mechanisms related thereto.

Mice were orally administered with DSS for 1 week and then additional with drinking water for 3 days, and comparison was made on a group induced with enteritis and a group administered simultaneously with DSS and bacterial strains for 1 week and additionally with bacterial strains for 3 days.

The bacterial strain administered group consisted of a group administered with a single strain, a group administered in combination of two species of bacteria, and a group administered in combination of three species of bacteria. Administration was performed in a dosage of $1\times10^8$ cfu for *Eubacterium rectale,* $3.8\times10^8$ cfu for *Tetragenococcus halophilus*, and $3.9\times10^7$ cfu for *Lactobacillus animalis*. Dosing ratio of 1:3.8:0.39 was applied for each strain. A normal control was administered with drinking water. Mice were then used in the following experiments.

1) Checking of Weight Changes in a DSS-Induced Enteritis Mouse Model and Weight Changes in a Group Administered with Strains As a result of checking the weight changes in DSS-administered mice, as shown in FIG. 1, the weight of the DSS-administered mice decreased to a statistically significant level ($p=0.001$), but there was no significant decrease in the body weight in control mice and a group administered with DSS and bacterial strains. 10 days after administration, there was a statistically significant increase in the body weight compared to the DSS-administered group.

Figure 2:
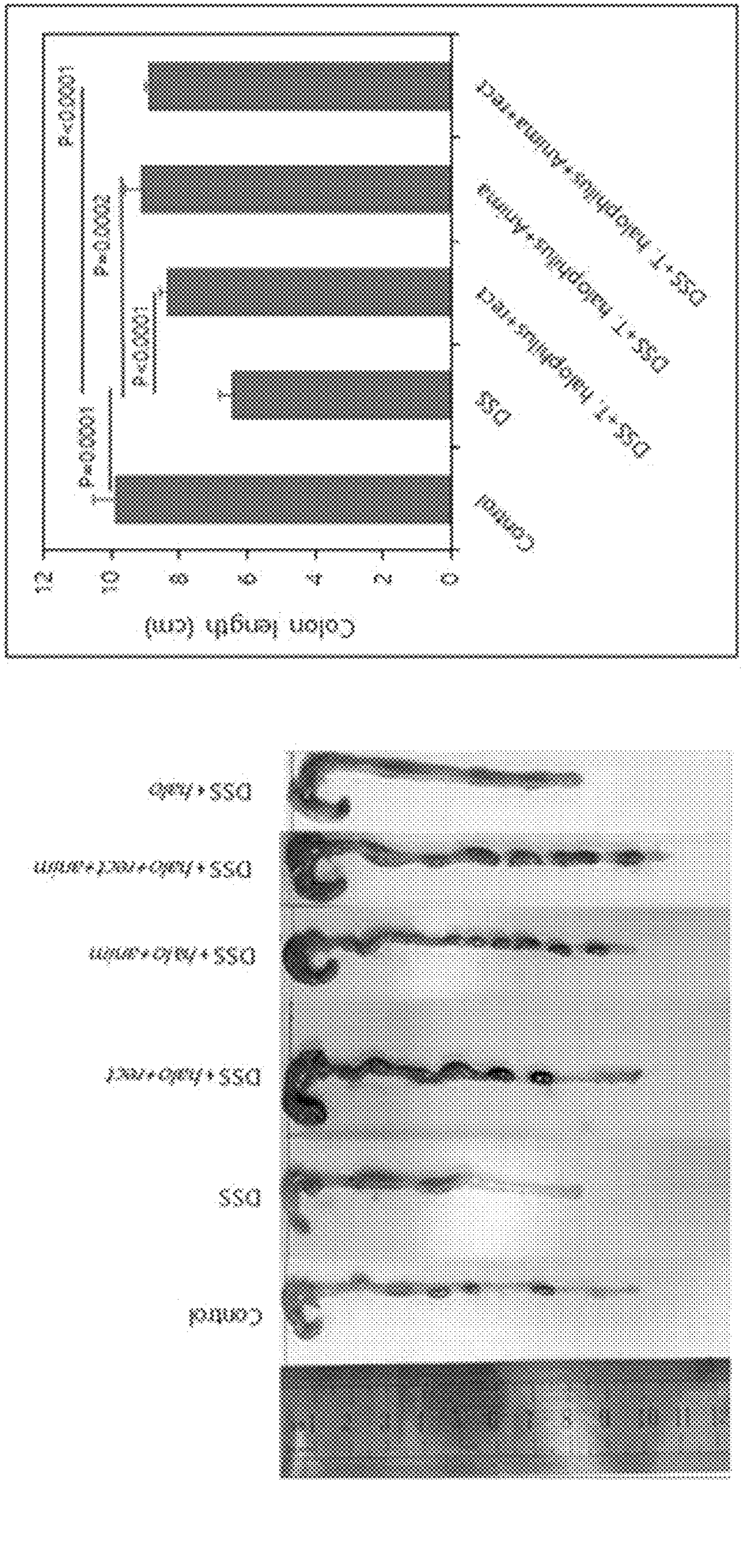
FIG. 2 shows comparison of a colon length of a DSS-induced enteritis mouse model according to an example embodiment of the present disclosure.

2) Comparison of the Colon Length in the DSS-Induced Enteritis Mouse Model and the Group Administered with Strains As a result of checking the colon length of DSS-administered mice, as shown in FIG. 2, the length of colon decreased in the DSS-induced enteritis mouse model, but, in the case when the bacterial strain was administered, the colon length increased statistically significantly and recovered.

Figure 3:
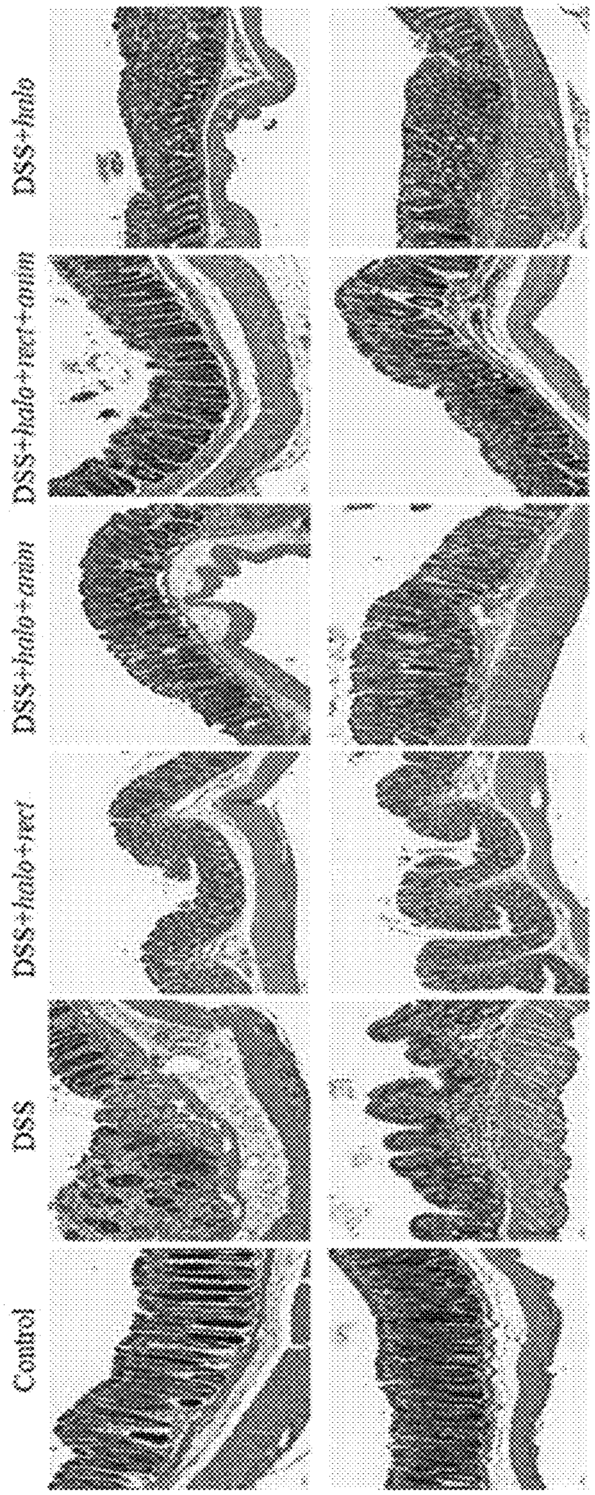
FIG. 3 shows changes in intestinal tissues of a DSS-induced enteritis mouse model according to an example embodiment of the present disclosure.

3) Comparison of Histology of Intestinal Tissues in the DSS-Induced Enteritis Mouse Model and a Group Administered with Bacterial Strains As a result of comparing the shape of intestinal tissues of DSS-administered mice, as shown in FIG. 3, compared to the DSS-induced enteritis mouse model, it was found that the shape of intestinal tissues of a group administered with three species of strains was maintained at the level that is the most comparable to that of normal mice.

Figure 4:
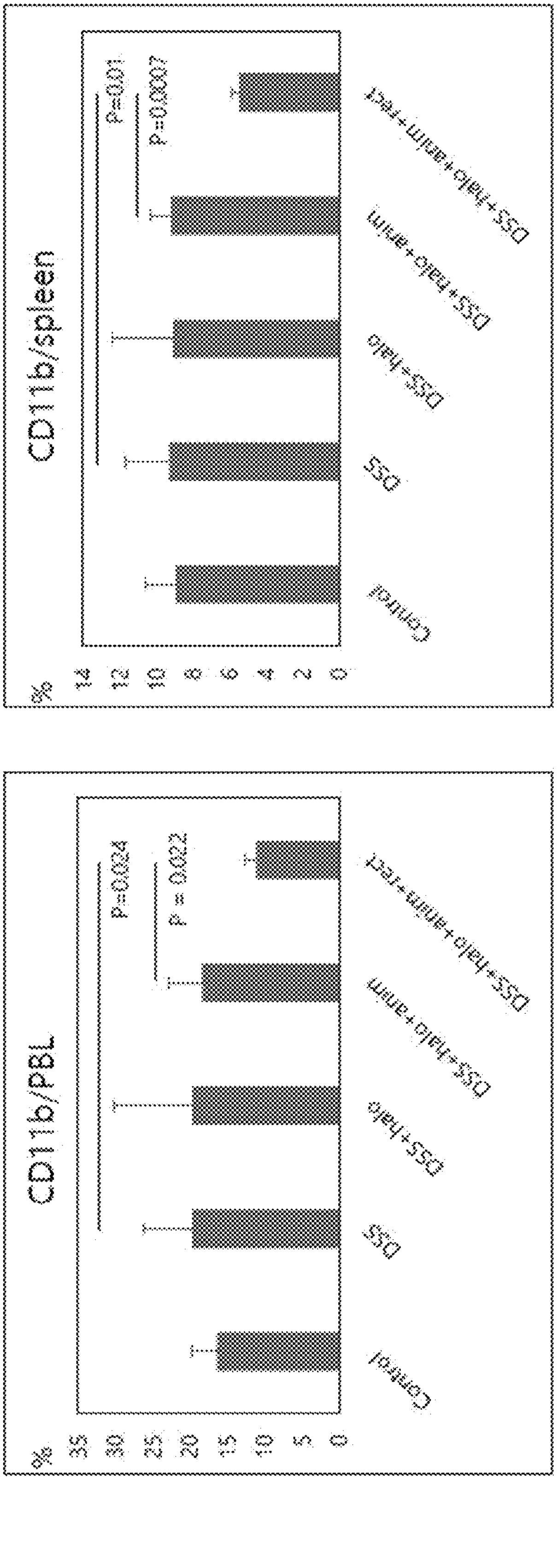
FIG. 4 shows changes in the frequency of CD11b+ cells in a DSS-induced enteritis mouse model according to another example embodiment of the present disclosure. (PBL: Peripheral blood lymphocytes/spleen)

<Example 3> Identification of Immunomodulatory Effects on an Inflammatory Bowel Disease 1) CD11 is involved in adhesion and inflammation among cells such as monocytes, macrophages, natural killer (NK) cells, and granulocytes. Referring to FIG. 4, the frequency of CD11b+ cells decreased in the group simultaneously administered with three species of strains among the DSS-induced enteritis mouse models.

Figure 5:
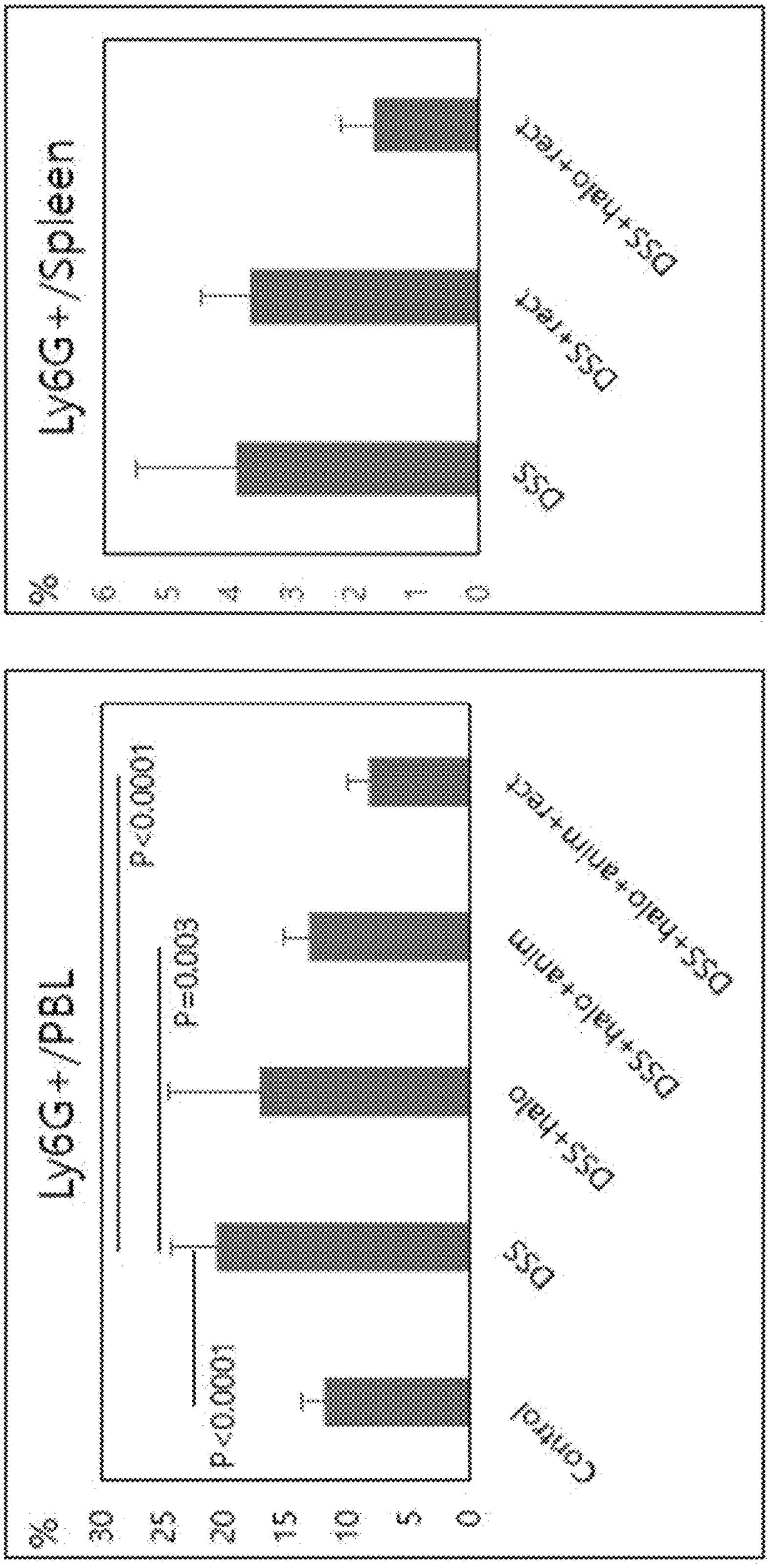
FIG. 5 shows changes in the frequency of Ly6G+ cells in a DSS-induced enteritis mouse model according to another example embodiment of the present disclosure.

2) Lymphocyte antigen 6 complex locus G6D (Ly6G) is a marker of monocytes, granulocytes, and neutrophils. Referring to FIG. 5, it was observed that Ly6G+ granulocytes increased in the DSS-induced enteritis mouse model, and the frequency of Ly6G+ cells decreased the most effectively when two or three species of bacterial strains were administered.

Figure 6:
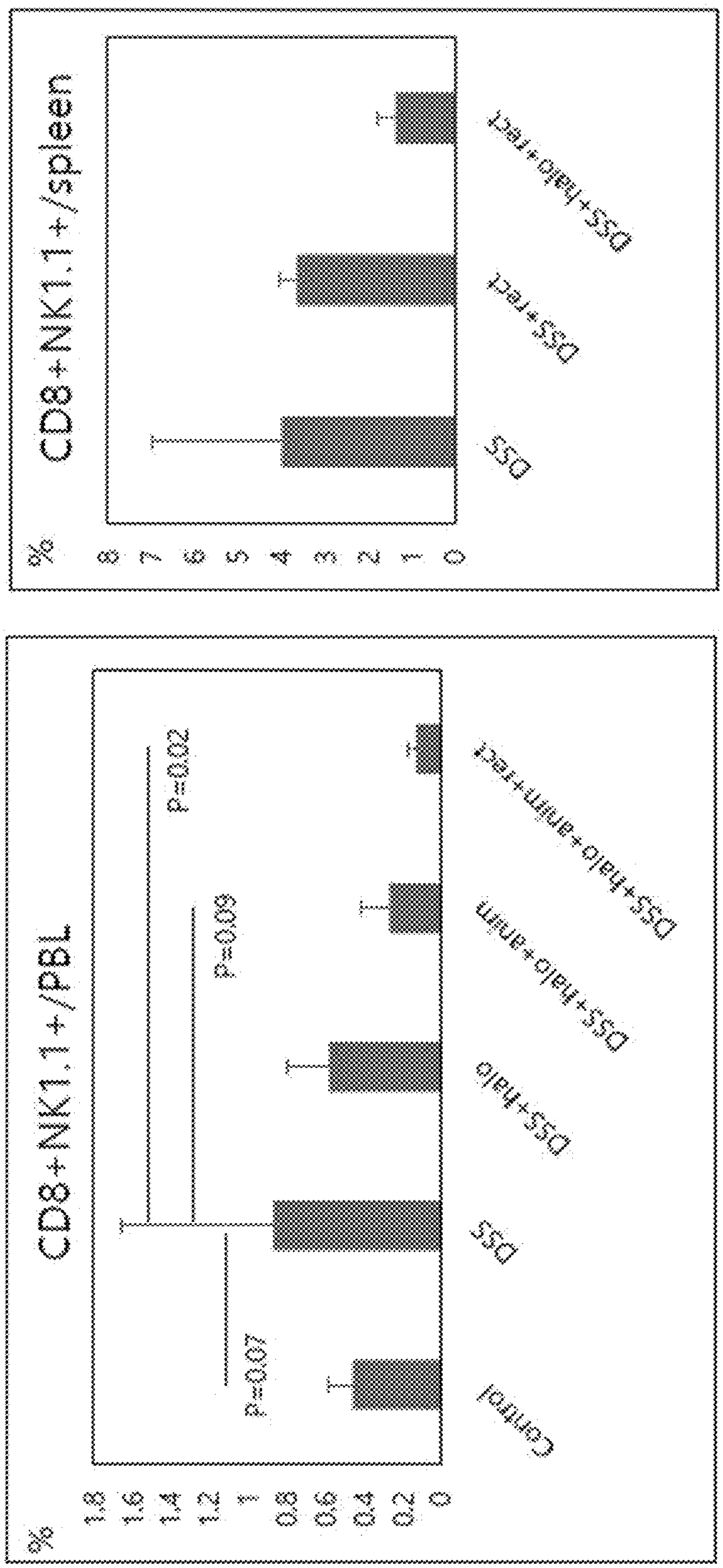
FIG. 6 shows changes in the frequency of CD8+NK1.1+ cells in a DSS-induced enteritis mouse model according to another example embodiment of the present disclosure.
Figure 8:
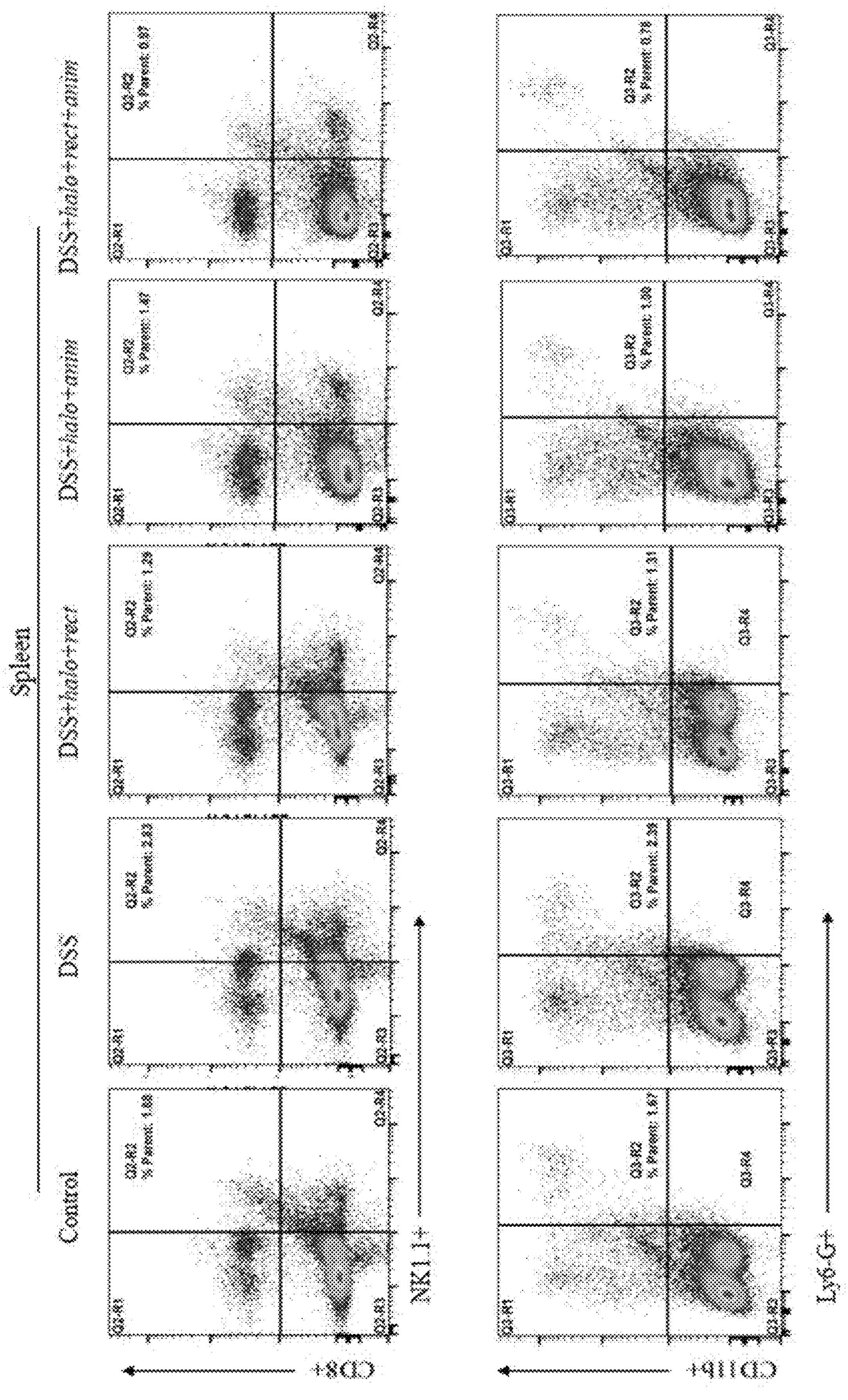
FIG. 8 shows changes in the frequency of cells in the FIGS. 6 and 7 in the spleen of the mouse model.

3) CD8+NK1.1+ cells play pathogenic roles and are known to be a main target in the disease control. Referring to FIGS. 6 and 8, the frequency of CD8+NK1.1+ cells increased in the DSS-induced enteritis mouse model, but that of CD8+NK1.1+ cells decreased in the group administered with two or three species of strains, while a significant decrease was observed especially in the group administered with three species of strains.

Figure 7:
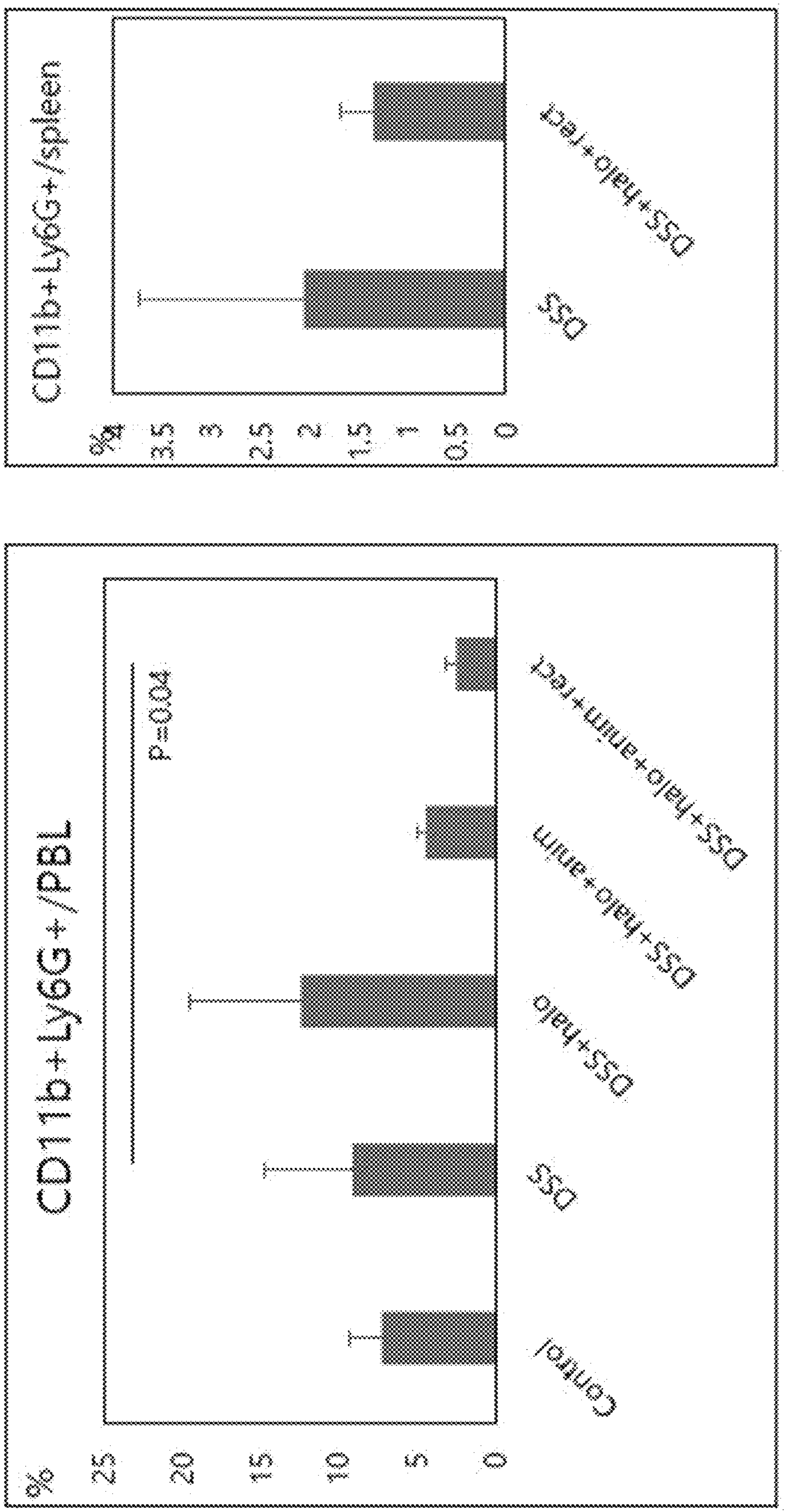
FIG. 7 shows changes in the frequency of CD11b+Ly6G+ cells in a DSS-induced enteritis mouse model according to another example embodiment of the present disclosure.

4) CD11b+Ly6G+ cells are used as a marker for neutrophils, and an increase in the number of neutrophils is a feature of the inflammatory response. Referring to FIGS. 7 and 8, the frequency of CD11b+Ly6G+ cells increased in the DSS-induced enteritis mouse model, but that of these cells decreased in the group administered with two or three species of strains, while the most significant decrease was observed especially in the group administered with three species of strains.

Figure 9:
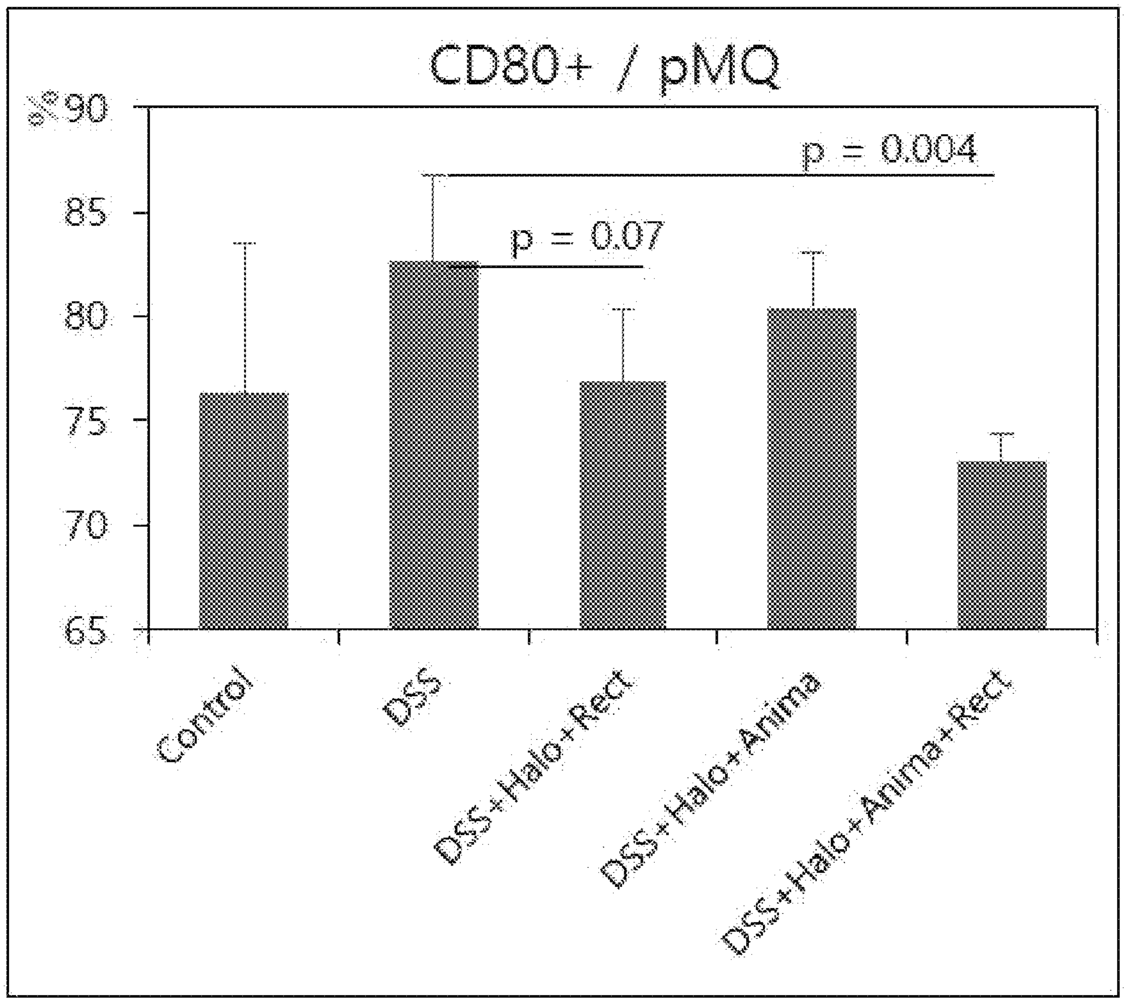
FIG. 9 shows changes in the frequency of CD80+ cells in a DSS-induced enteritis mouse model according to another example embodiment of the disclosure. (pMQ: peritoneal macrophages)

5) In the colorectal mucosa with Crohn's disease and ulcerative colitis, it is known that the frequency of CD80+ cells significantly increases compared to controls while that of CD80+ cells decreases during the remission of the DSS-induced enteritis mouse models. Referring to FIG. 9, the frequency of CD80+ cells significantly decreased among intraperitoneal cells in the group administered with three species of strains in the DSS-induced enteritis mouse model.

As described above, as a specific part of the present disclosure has been described in detail, it is apparent to those skilled in the art that such specific descriptions are only preferred embodiments, and the scope of the present disclosure is not limited thereby. In other words, the substantial scope of the present disclosure is defined by the appended claims and their equivalents.

The invention claimed is:

1. A pharmaceutical composition for preventing or treating an inflammatory bowel disease, comprising, as active ingredients, a mixture of species comprising *Tetragenococcus halophilus, Eubacterium rectale*, and *Lactobacillus animalis*; or cultures of the mixture, concentrates of the cultures, extracts of the cultures, or lysates of the cultures, wherein a mixing ratio of *Eubacterium rectale:Tetragenococcus halophilus:Lactobacillus animalis* is 1:3.8:0.39.

2. The pharmaceutical composition of claim 1, wherein the composition reduces one or more immune cells whose phenotypes are selected from the group consisting of CD11 b+, Ly6G+, CD8+NK1.1+, CD11b+Ly6G+, and CD80+.

3. The pharmaceutical composition of claim 1, wherein the inflammatory bowel disease is one or more selected from the group consisting of ulcerative colitis, Crohn's disease, Behcet's enteritis, infectious enteritis, radiation enteritis, ischemic bowel disease, and irritable bowel syndrome.

4. A health food composition for preventing or ameliorating an inflammatory bowel disease, comprising, as active ingredients, a mixture of species comprising *Tetragenococcus halophilus, Eubacterium rectale*, and *Lactobacillus animalis*; or cultures of the mixture, concentrates of the cultures, extracts of the cultures, or lysates of the cultures, wherein a mixing ratio of *Eubacterium rectale:Tetragenococcus halophilus:Lactobacillus animalis* is 1:3.8:0.39.

5. The health food composition of claim 4, wherein the inflammatory bowel disease is one or more selected from the group consisting of ulcerative colitis, Crohn's disease, Behcet's enteritis, infectious enteritis, radiation enteritis, ischemic bowel disease, and irritable bowel syndrome.

* * * * *